United States Patent [19]
Sato et al.

[11] Patent Number: 5,188,113
[45] Date of Patent: Feb. 23, 1993

[54] ULTRASONIC DIAGNOSIS APPARATUS

[75] Inventors: Takeshi Sato, Tochigi; Sumiko Saito, Ootawara, both of Japan

[73] Assignee: Kabushiki Kaisha Toshiba, Kawasaki, Japan

[21] Appl. No.: 680,163

[22] Filed: Apr. 3, 1991

[30] Foreign Application Priority Data

Apr. 4, 1990 [JP] Japan .................................. 2-89808
Oct. 11, 1990 [JP] Japan .................................. 2-270478

[51] Int. Cl.$^5$ .............................................. A61B 8/12
[52] U.S. Cl. ........................... 128/661.09; 128/660.05; 128/661.08; 73/861.25
[58] Field of Search ...................... 128/661.07, 661.08, 128/661.09, 660.05, 661.10; 73/861.25, 631, 602

[56] References Cited

U.S. PATENT DOCUMENTS

| | | | |
|---|---|---|---|
| 4,817,617 | 4/1989 | Takeuchi et al. | 128/660.05 |
| 4,930,514 | 6/1990 | Baba et al. | 128/661.09 |
| 4,932,413 | 6/1990 | Angelsen et al. | 128/661.09 |
| 4,955,386 | 9/1990 | Nishiyama et al. | 128/6661.09 |
| 4,993,418 | 2/1991 | Weaver et al. | 128/661.08 |

*Primary Examiner*—William E. Kamm
*Assistant Examiner*—George Manuel
*Attorney, Agent, or Firm*—Finnegan, Henderson, Farabow, Garrett and Dunner

[57] ABSTRACT

An ultrasonic diagnosis apparatus comprises an ultrasonic probe for scanning ultrasonic waves in a cross-sectional area of a subject, and receiving the reflected ultrasonic waves, a B-mode processor for detecting the intensity of the reflected ultrasonic waves, thereby obtaining tomographic images of the subject, an MTI processor for detecting a Doppler shift of the reflected waves, thereby obtaining blood flow data representing the velocity and direction of blood flow in the tomographic image, and a coloring processing circuit for receiving the outputs of the B-mode processor and the MTI processor and coloring the blood flow part in a monochromatic tomographic image in accordance with the velocity and direction of the blood flow. A first digital scan converter is connected between the B-mode processor and the color processing circuit and a second digital scan converter is connected between the MTI processor and the color processing circuit. The first digital scan converter changes the scan direction for of the tomographic image and produces an interpolated tomographic image. The second digital scan converter changes the scan direction of scanning blood flow data, detects aliasing of blood data, and produces an interpolated blood flow data, the interpolation being controlled in accordance with the detection of aliasing.

19 Claims, 11 Drawing Sheets

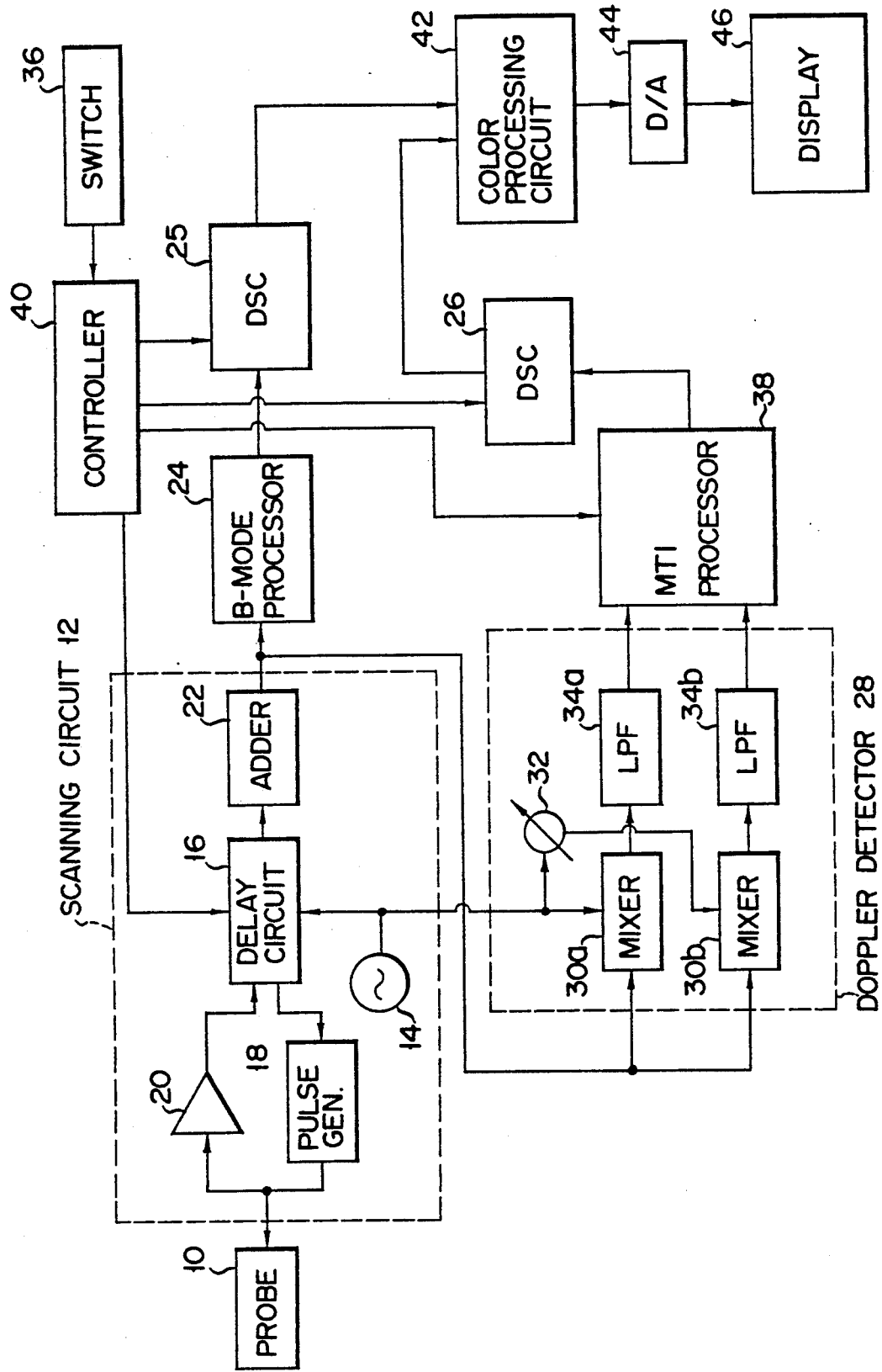
F I G. 1

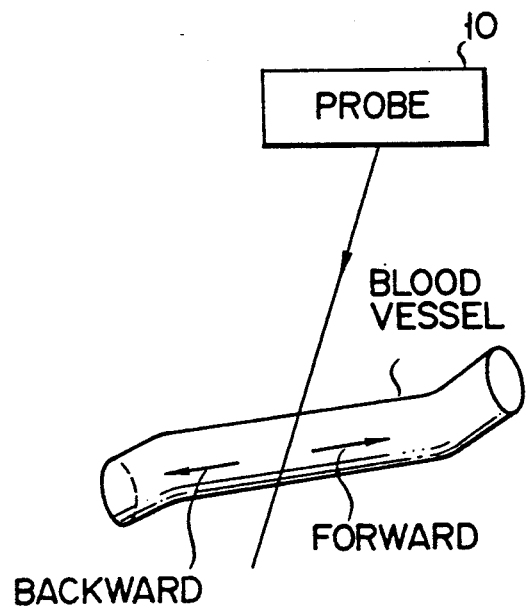
F I G. 6
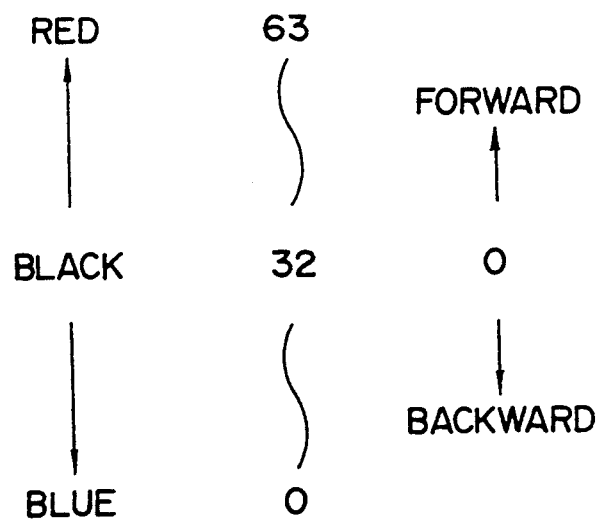
F I G. 7

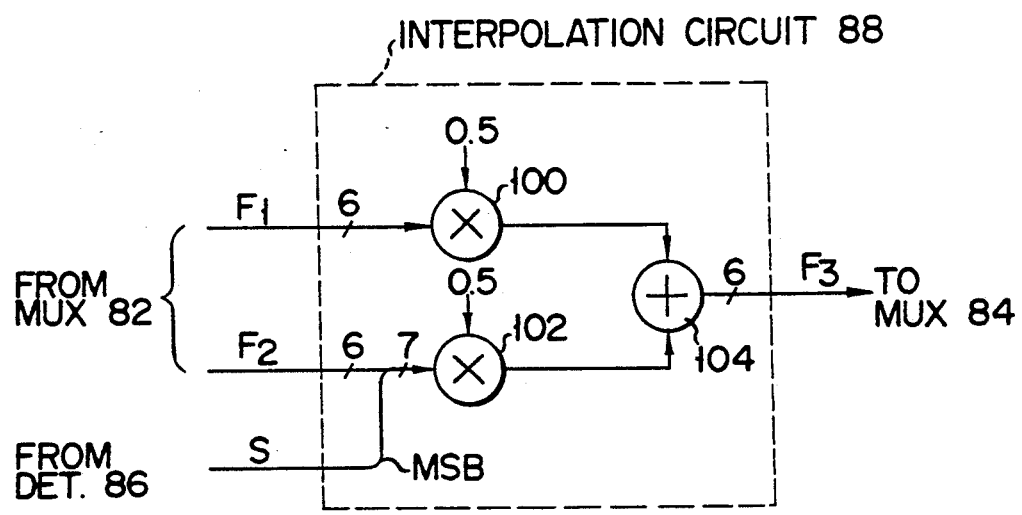
F I G. 10
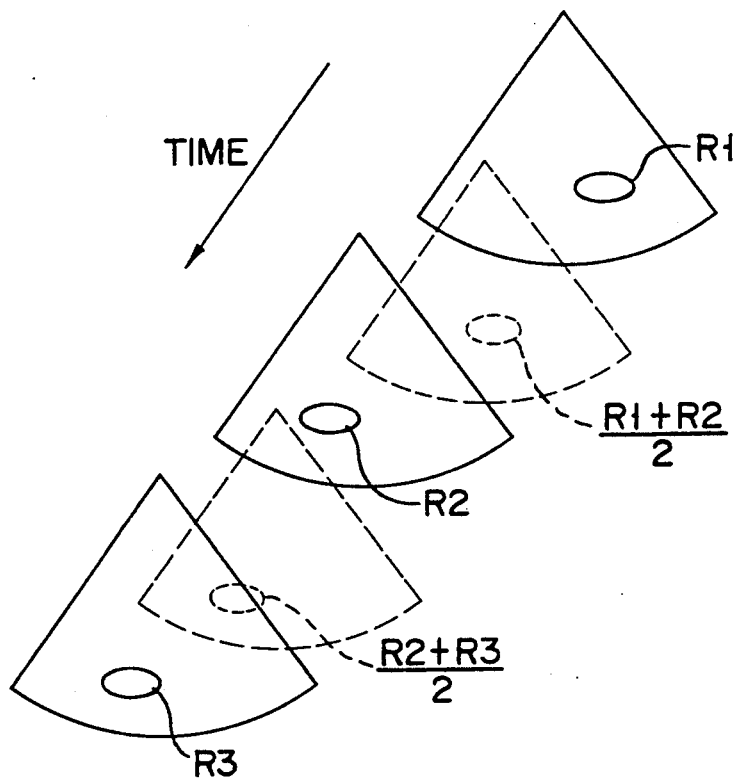
F I G. 11

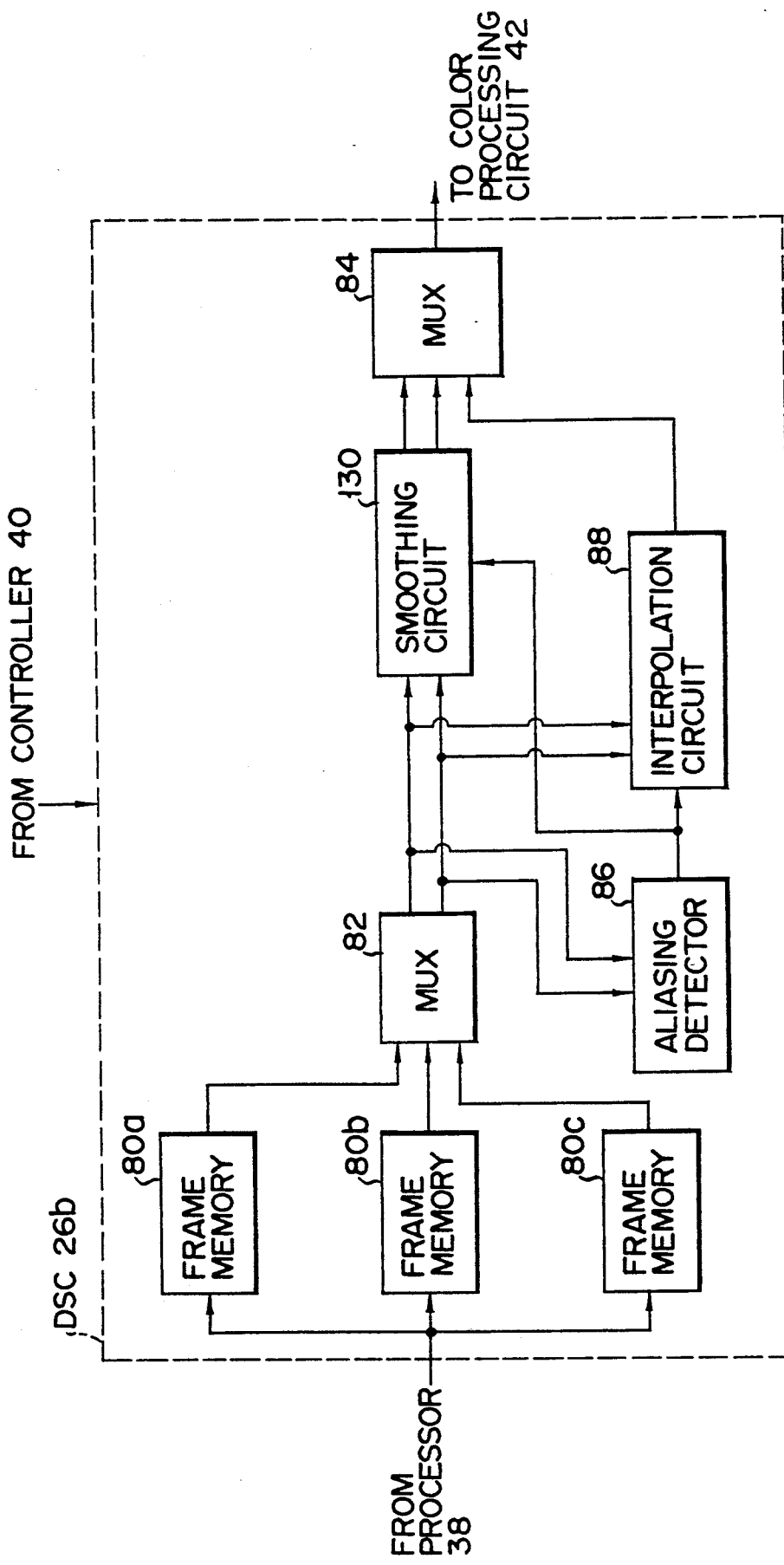
F I G. 15

ULTRASONIC DIAGNOSIS APPARATUS

BACKGROUND OF THE INVENTION

1. Field of the Invention

The present invention relates to an ultrasonic diagnosis apparatus for radiating ultrasonic waves in a cross section of a subject, detecting the intensity of reflected echo, and brightness-modulating the intensity of the reflected echo, thereby obtaining a tomogram of the subject, and also for detecting a frequency-deviation (Doppler shift) of the reflected echo and detecting the direction and flow velocity of a blood, flow in the subject, thereby displaying the blood flow two-dimensionally by coloring the blood flow portion in the tomogram in accordance with the detected flow velocity and direction.

2. Description of the Related Art known as a color Doppler flow mapping (CDF) apparatus, and in particular as a BDF apparatus, since it relates to a blood flow imaging in a B-mode display. A blood flow, which approaches an ultrasonic probe, is colored in red, a blood flow, which moves away from the probe, is colored in blue, and a turbulent flow is colored in green. The velocity of the blood flow is represented by brightness.

The BDF apparatus will now be described in brief. An ultrasonic Doppler method utilizes an ultrasonic Doppler shift wherein, when ultrasonic waves are reflected by a moving body, the frequency of the reflected waves shifts from a transmission frequency in proportion to the velocity of the object. Specifically, ultrasonic waves are radiated to a subject and the radiation direction is scanned in order to obtain a tomogram. In this case, ultrasonic pulses are transmitted repeatedly in respective directions in which ultrasonic waves are radiated, and a Doppler shift frequency is detected based on the phase variation of the reflected echo. Thus, the data representing the movement of the moving body at a depth, at which the echo is reflected, is acquired. According to the ultrasonic Doppler method, it is possible to know the direction of the blood flow at a location in the subject and the condition of the blood flow (e.g. turbulent flow or regular flow).

In order to obtain blood flow data from an ultrasonic reflected echo signal, an ultrasonic probe is driven to repeatedly radiate ultrasonic waves in a raster direction for a number of times, and the received signal is detected by an orthogonal phase detecting circuit, thereby obtaining a Doppler shift signal on the basis of blood cells. Since a color Doppler image is obtained in real time, the Doppler shift signal is frequency-analyzed by a frequency analyzing circuit to find an average value of Doppler shift, a variance value of Doppler shift, an average power of Doppler shift, etc. A blood flow velocity color flow mapping image is obtained by an auto-correlation circuit, etc. built in the frequency analyzing circuit, and two-dimensional blood data is displayed on a TV monitor. Recently, this apparatus has been used to diagnose not only the heart but also the part in which blood flow velocity is low, for example, blood vessel in the abdomen or peripheral blood vessel.

The conventional BDF apparatus, however, has the following problem. In order to obtain the two-dimensional blood flow data, as stated above, it is necessary to transmit and receive ultrasonic waves in one ultrasonic raster direction for a number of times. In addition, in order to observe the blood flow with a low velocity, it is necessary to continue observation for a long time in one radiation direction. Consequently, a long time is needed to acquire one BDF image. For example, when the blood flow in the abdomen is observed, a TV monitor is normally capable of displaying only four to ten frame images in every second.

On the other hand, about 30 frame images per second are necessary in order to enable a person to observe images smoothly and clearly, which are displayed on a monitor employing a standard TV system such as NTSC. The above-mentioned four to ten frame images per second result in discontinuity and unclearness in images.

SUMMARY OF THE INVENTION

An object of the present invention is to provide an ultrasonic diagnosis apparatus capable of obtaining a smooth and clear ultrasonic blood flow image.

According to the present invention, there is provided an ultrasonic diagnosis apparatus comprising:

ultrasonic wave transmitting/receiving means for scanning a subject with ultrasonic waves, and receiving the reflected ultrasonic waves;

image producing means for detecting the intensity and Doppler shift of the reflected ultrasonic waves, thereby producing color flow mapping images, the color flow mapping images being produced by coloring a blood flow in a tomographic image of the subject in accordance with Doppler shift;

detecting means for detecting aliasing on the basis of a change in Doppler shift in the color flow mapping images of two frames; and interpolating means for interpolating an intermediate frame based on two frames of the color flow mapping images, thereby increasing a display repetition rate of the color flow mapping images, wherein the frame-interpolating processing varies depending on the aliasing detection result of the detecting means.

According to the ultrasonic diagnosis apparatus of the present invention, a color flow mapping image obtained by detecting the intensity and Doppler shift of the reflected ultrasonic waves is frame-interpolated, thereby increasing the display frame rate of color flow mapping images and realizing natural dynamic display. In addition, since an aliasing of blood flow data is detected, if the aliasing has occurred, the frame interpolation is carried out with the aliasing taken into account. Therefore, appropriate frame interpolation can be performed.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 1 is a block diagram showing an ultrasonic diagnosis apparatus according to a first embodiment of the present invention;

FIG. 6 is a view for defining the direction of blood flow;

FIG. 7 is a view for explaining the relationship between the direction of blood flow and the display color;

FIG. 10 is a block diagram showing in detail an interpolation circuit according to the first embodiment;

FIG. 11 shows the result of interpolation according to the first embodiment;

FIG. 15 is a block diagram showing in detail a blood flow data DSC which constitutes a main part of a third embodiment of the invention;

DETAILED DESCRIPTION OF THE PREFERRED EMBODIMENTS

Figure 2:
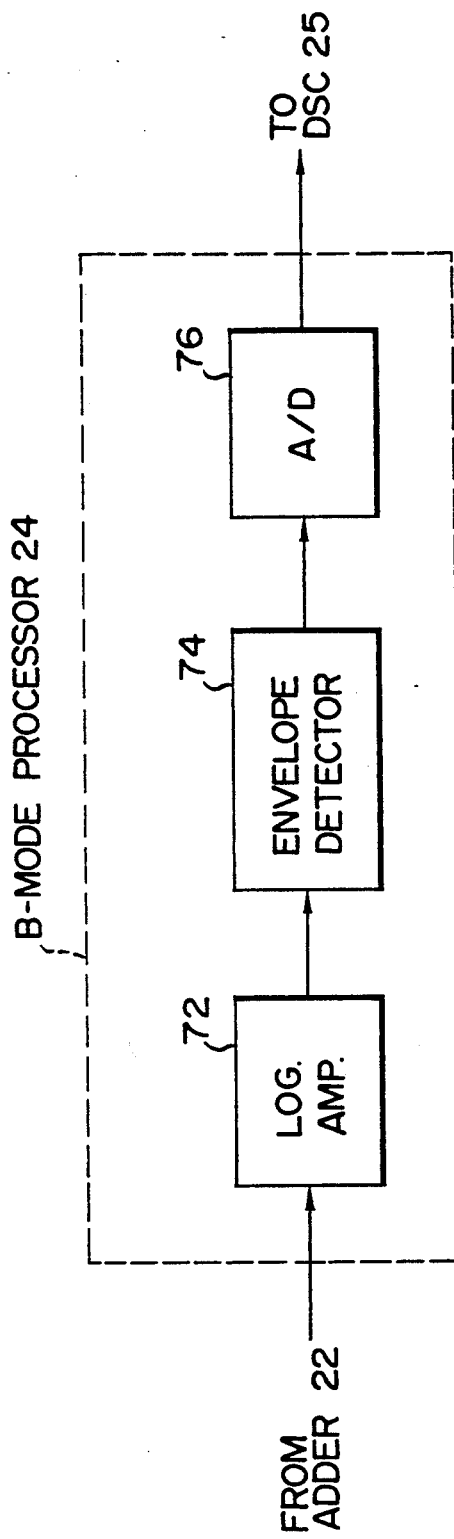
FIG. 2 is a block diagram showing in detail a B-mode processor according to the first embodiment.

An ultrasonic diagnosis apparatus according to a preferred embodiment of the present invention will be described with reference to the accompanying drawings. In FIG. 1, a scanning circuit 12 is connected to an electronic sector scanning type ultrasonic probe 10. The probe 10 comprises a large number of piezoelectric transducers arrayed in a row. By varying the timing of applying of voltages to the respective transducers, it is possible to cause ultrasonic waves to scan a sector or focus the ultrasonic waves. The probe 10 need not be limited to the electronic sector scanning type and it may be of a linear scanning type or a mechanical scanning type.

In the scanning circuit 12, an output of an oscillator 14, which determines an oscillation frequency of the ultrasonic transducers, is applied to the probe 10 via a delay circuit 16 and a pulse generator 18. The pulse generator 18 periodically supplies the probe 10 with driving pulses. The inverse of the period is the repetition frequency (rate frequency) of the ultrasonic waves. The delay circuit 16 comprises a large number of delay lines having variable delay times. The outputs of the delay lines are coupled to the respective transducers. By varying the delay times of the respective delay lines, it becomes possible to vary the directions (raster directions) of the ultrasonic waves transmitted from the probe 10. The delay times are controlled by control signals from a controller 40. In order to detect a Doppler shift, it is necessary to transmit ultrasonic waves in the same raster direction for several times. Thus, in this embodiment, ultrasonic waves are radiated several times in each of the raster directions, and then the raster direction is changed by one.

An output from the probe 10 is supplied to an adder 22 through a preamplifier 20 and the delay circuit 16. In this case, the outputs from the respective transducers are supplied to the adder 22 through the delay lines, with the same delay times as in the transmission mode. An output from the adder 22 is input to a B-mode processor 24, and the intensity of the reflected ultrasonic wave in each raster direction is detected. The B-mode processor 24 has a structure as shown in FIG. 2, and comprises a logarithmic amplifier 72, an envelope detector 74, and an A/D converter 76. The logarithmic amplifier 72 logarithmic-amplifies a received signal output from the adder 22, and the envelope detector 74 detects an envelope of the signal from the amplifier 72. An output from the B-mode processor 24 is input to a first digital scan converter (DSC) 25 as brightness data of each raster, that is, B-mode image (tomogram) data. The raster of the ultrasonic probe 10 is changed in a sectorial fashion, but the raster of a monitor (display) 46 is lateral, as in a standard TV system. Thus, the DSC 25 alters the raster direction (scan direction) of the input image and outputs the resultant image. Though not shown, the DSC 25 comprises frame memories for storing image data of at least two frames and an interpolating circuit for interpolating an image data of an intermediate frame.

An output from the adder 22 and an output from the oscillator 14 are supplied to a Doppler detector 28. The Doppler detector 28 is a circuit for detecting the Doppler shift frequency by an orthogonal detection method. The Doppler detector 28 comprises mixers 30a and 30b, a 90° phase shifter 32, and low-pass filters (LPF) 34a and 34b. An output from the adder 22 is multiplied by an output from the oscillator 14 in the mixer 30a and the output from the adder 22 is multiplied by an output from the phase shifter 32 in the mixer 30b. Each of the mixers 30a and 30b outputs a doppler shift frequency component and a high-frequency component (double the transmission frequency). The LPFs 34a and 34b remove high-frequency components from the outputs from the mixers 30a and 30b. The outputs from the LPFs 34a and 34b are a cosine component and a sine component of the Doppler shift frequency. The Doppler shift frequency is provided with two channels for cosine and sine components, in order to detect the polarity of the shift frequency.

Figure 3:
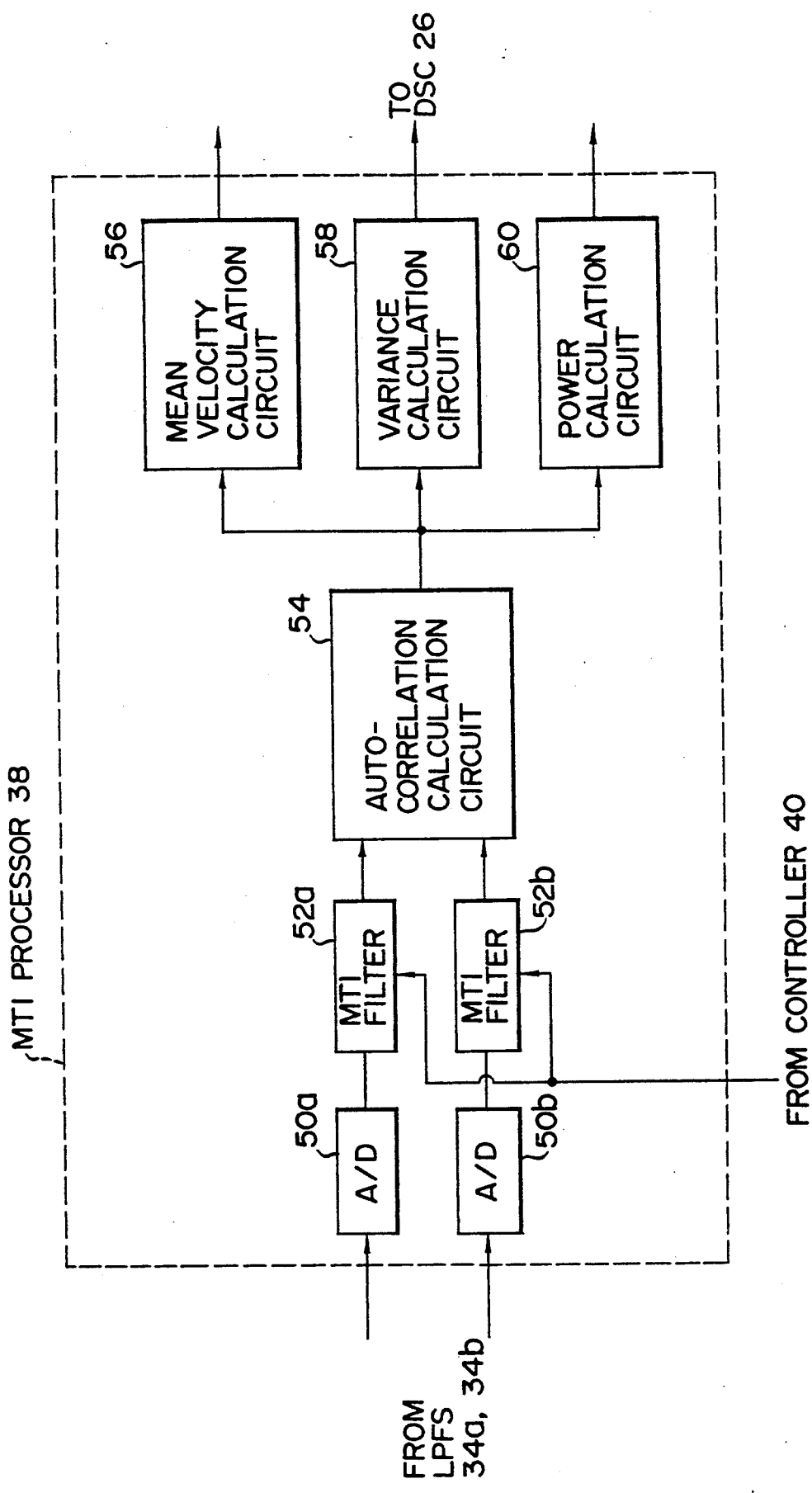
FIG. 3 is a block diagram showing in detail an MTI processor according to the first embodiment.

The output from the Doppler detector 28 is supplied to an MTI (Moving Target Indicator) processor 38 for color Doppler flow mapping. FIG. 3 is a block diagram showing the MTI processor 38 in detail. The outputs from the LPFs 34a and 34b are supplied to an auto-correlation calculation circuit 54 through A/D converters 50a and 50b and MTI filters 52a and 52b. The auto-correlation calculation circuit 54 is employed to perform, in real time, frequency analysis of many points distributed two-dimensionally. Compared to an FFT process, the number of arithmetic operations decreases. The output from the auto-correlation calculation circuit 54 is supplied to a mean velocity calculation circuit 56, a variance calculation circuit 58, and a power calculation circuit 60. The outputs from the calculation circuits 56, 58 and 60 are supplied to a second DSC 26. Thus, the MTI processor 38 can acquire blood flow data at each point on a tomogram obtained by the B-mode processor 24.

The MTI filters 52a and 52b function to remove unnecessary reflected waves (clutter component) from a stationary reflector (blood vessel wall, heart wall, etc.). The filters 52a and 52b comprise digital filters having low-pass characteristics. Specifically, the MTI filters 52a and 52b detect the movement of blood flow on the basis of the phase variation, with respect to the same pixel, between the echo signals obtained by the several-time ultrasonic radiation in the same raster direction, and remove the clutter component. Alternatively, the MTI filters may have an analog construction and be composed of delay lines and subtracters for subtracting, from the reflected signals, the reflected signals obtained after a predetermined time period, thereby removing the clutter component.

A mean value v of Doppler shift frequency, a variance $\sigma^2$, and total power TP respectively output from the mean velocity calculation circuit 56, variance calculation circuit 58, and power calculation circuit 60 are supplied to the DSC 26 for blood flow data. The total power TP is proportional to the intensity scattered echo from blood flow, but echo from a moving body having a frequency not higher than the cut-off frequency of the MTI filters 52a and 52b is removed. Like the DSC 25, the DSC 26 alters the scanning direction of the input blood flow data and outputs the resultant data, and, where necessary, performs frame interpolation. The details of the DSC 26 will be described later.

Control signals from the controller 40 are also supplied to the MTI processor 38, DSC 25, and DSC 26. A manual switch 36 is connected to the controller 40. The monochromatic tomogram and blood flow data, which are output from the DSCs 25 and 26, are supplied to a color processing circuit 42. As in the conventional art, the blood flow portion in the tomogram is colored such that the direction of the blood flow towards the probe is expressed in red, the direction away from the probe is in blue, the mean velocity is in brightness, and the velocity distribution is expressed by hues (mixed with green), thereby producing a color Doppler image. The output from the color processing circuit 42 is supplied to the display 46 through a D/A converter 44. Though not shown, the output from the D/A converter 44 may be supplied to a recording section such as a VTR.

Figure 4:
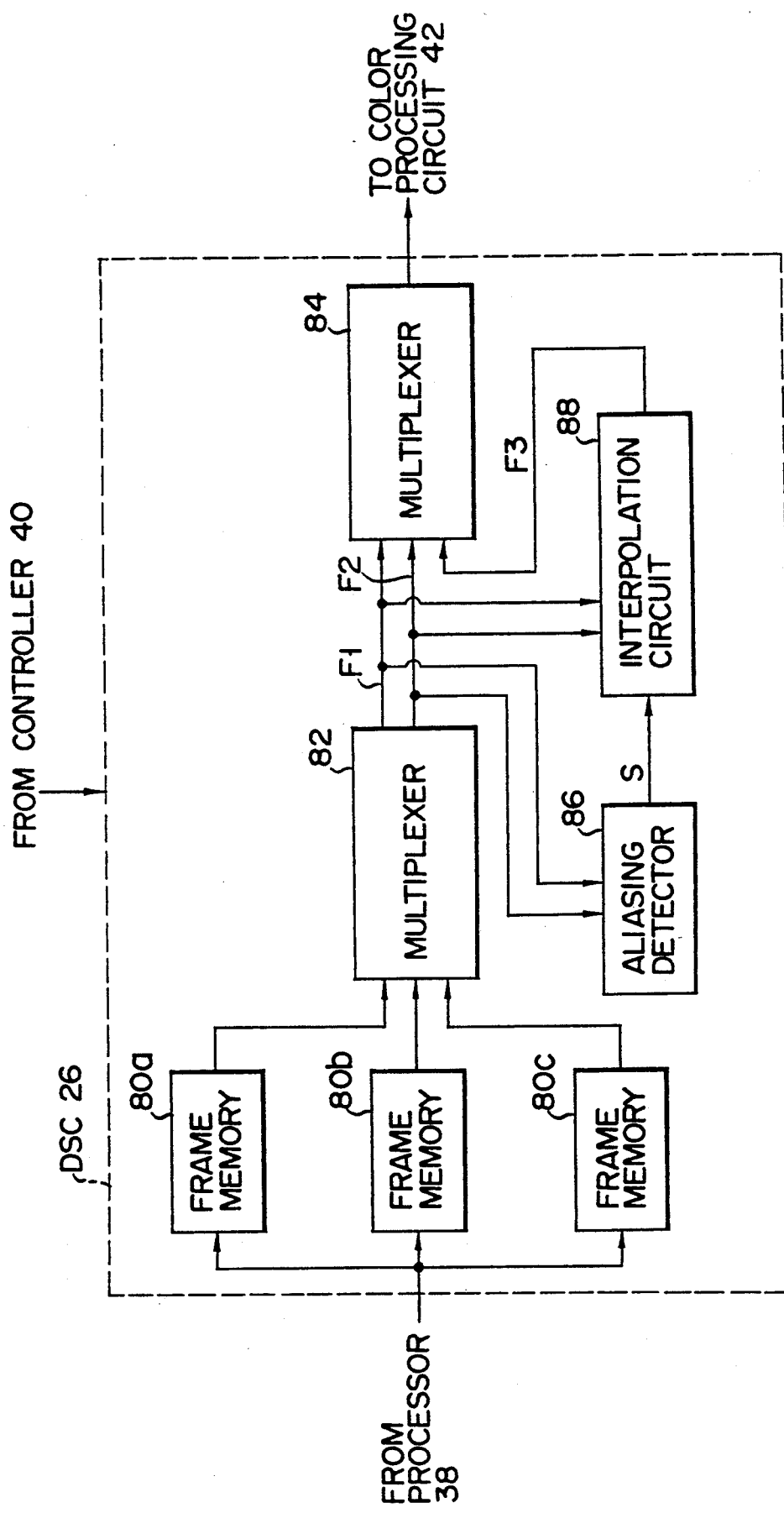
FIG. 4 is a block diagram showing in detail a blood flow data DSC according to the first embodiment.

The features of the present invention will now be described. FIG. 4 is a block diagram showing in detail the second DSC 26 for blood flow data. The DSC 26 comprises three frame memories 80a, 80b, and 80c, multiplexers (MUX) 82 and 84 functioning as control means, an aliasing detector 86 functioning as determining means, and an interpolation circuit 88 functioning as interpolation means. The first DSC 25 for tomogram data has the same construction as the second DSC 26, except that the aliasing detector 86 is omitted.

Figure 5:
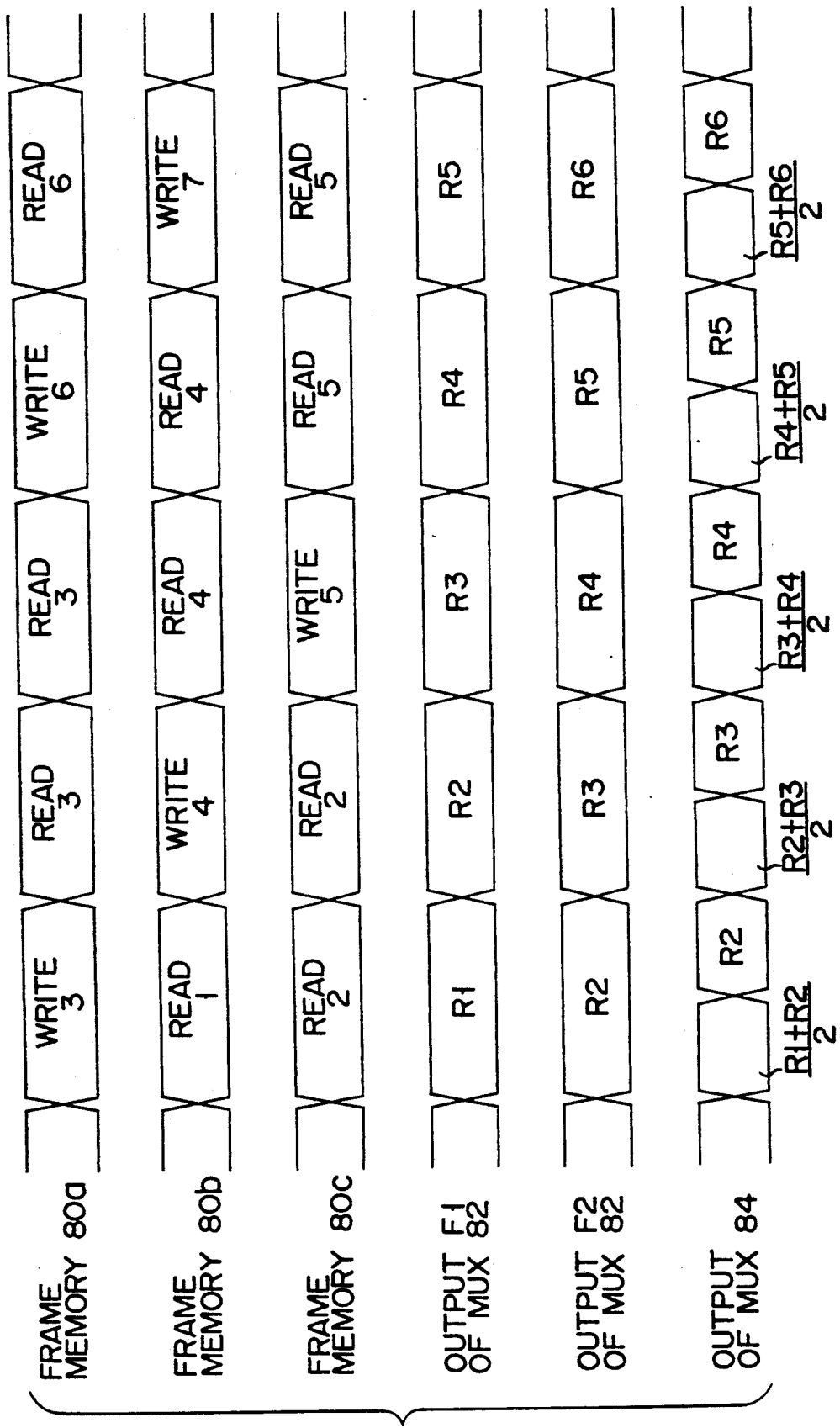
FIG. 5 is a timing chart illustrating the operation of the DSC shown in FIG. 4.

The three frame memories 80a to 80c are controlled by control signals from the controller 40, and store blood flow data supplied successively in units of a frame, as is shown in FIG. 5. The scanning direction is changed by altering the scan sequence of write and read. In FIG. 5, "WRITE 3" denotes a period for writing third-frame data, and "READ 3" denotes a period for reading third-frame data. In this manner, the blood flow data of each frame is successively written in the frame memories 80a to 80c. While one frame memory is set in the write mode, the other two frame memories are set in the read mode. Thus, the blood flow data of the same frame is read from each frame memory for a two-frame period. The outputs from the frame memories 80a to 80c are supplied to the three-input/two-output multiplexer 82. The multiplexer 82 delivers the outputs of the frame memories set in the read mode as first and second output signals F1 and F2. Thus, as is shown in FIG. 5, the output signals F1 and F2 of the multiplexer 82 are, respectively, the data of the second frame prior to the presently written frame, and the data of the first frame prior to the present frame, i.e., the prior frame. For example, in the period in which the third-frame data is written in the frame memory 80a, the first-frame and second-frame data are read out from the frame memories 80b and 80c and the read-out data are output from the multiplexer 82 as first and second signals F1 and F2.

The two outputs from the multiplexer 82 are supplied to the three-input/one-output multiplexer 84, aliasing detector 86, and interpolation circuit 88. The output from the aliasing detector 86 is delivered to the interpolation circuit 88, and the output from the interpolation circuit 88 is supplied to a third input terminal of the multiplexer 84. The outputs F1 and F2 from the multiplexer 82 are supplied to first and second input terminals of the multiplexer 84.

Figure 8:
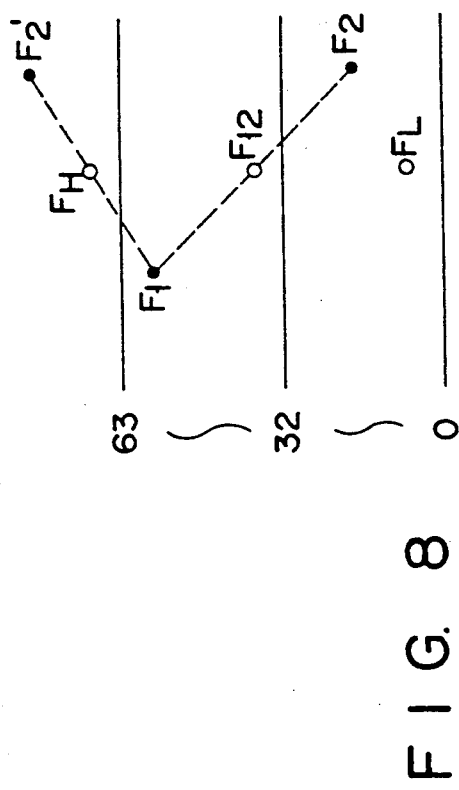
FIG. 8 illustrates the principle of interpolation in the case where aliasing is occurred.

The aliasing detector 86 will now be described. As is shown in FIG. 6, the direction of blood flow in a blood vessel is defined such that the direction towards the ultrasonic probe 10 is a forward direction, and the direction away from the probe 10 is a backward direction. As is shown in FIG. 7, the blood flow data velocity data is expressed in 6 bits (0 to 63). The center value 32 of the velocity data represents the velocity of 0, the velocity 0 to 32 indicates the velocity of backward flow (colored blue), and the velocity 32 to 63 indicates the velocity of forward flow (colored red). FIG. 8 is a view for explaining the aliasing due to blood flow. In the MTI processor 38, the repetition frequency fr of ultrasonic pulses is a sampling frequency; thus, a Doppler shift frequency fd, which can be detected by the sampling theorem, is limited as follows:

$$fd \leq |fr/2|$$

Thus, the upper-limit absolute value $|V_{max}|$ of the velocity, which is measurable, is given by:

$$|V_{max} = C \cdot fr/(4\cos\theta \cdot fo)$$

where C is the velocity of ultrasonic waves, of is a transmission frequency of ultrasonic waves, and $\theta$ is an angle defined by the line of movement of blood flow and the line of direction of radiated ultrasonic waves.

Thus, the velocity of flow, which exceeds fr/2, is decreased by "−fr", and so-called aliasing occurs. For example, as is shown in FIG. 8, velocity data F2' above 63 is found as velocity data F2 which is obtained by subtracting 63 from F2'. Where no aliasing is occurred, both velocity data F1 and F2 are within the range of 0 to 63; thus, the interpolation data of data F1 and F2 is data $F_{12}$ (=(F1+F2)/2). However, where aliasing has occurred, velocity data F2 is actually velocity data F2'; thus, genuine interpolation data is not $F_{12}$, but $F_L = F_H$ (=(F1+F2')/2)−63. In this way, in accordance with the occurrence/non-occurrence of aliasing, the interpolation processing for velocity data must be changed.

To solve the above problem, the aliasing detector 86 compares velocity data F1 and F2 supplied from the multiplexer 82, and, when an absolute value of the difference therebetween is greater than a threshold level and the polarities of the data F1 and F2 are different from each other, it is determined that the aliasing has occurred. Then, an aliasing detection signal S is output to the interpolation circuit 88. In this case, a suitable threshold level is about ⅜ of the full range of the velocity data, and where the velocity data is expressed in 6 bits, =63), 24 is suitable.

Figure 9:
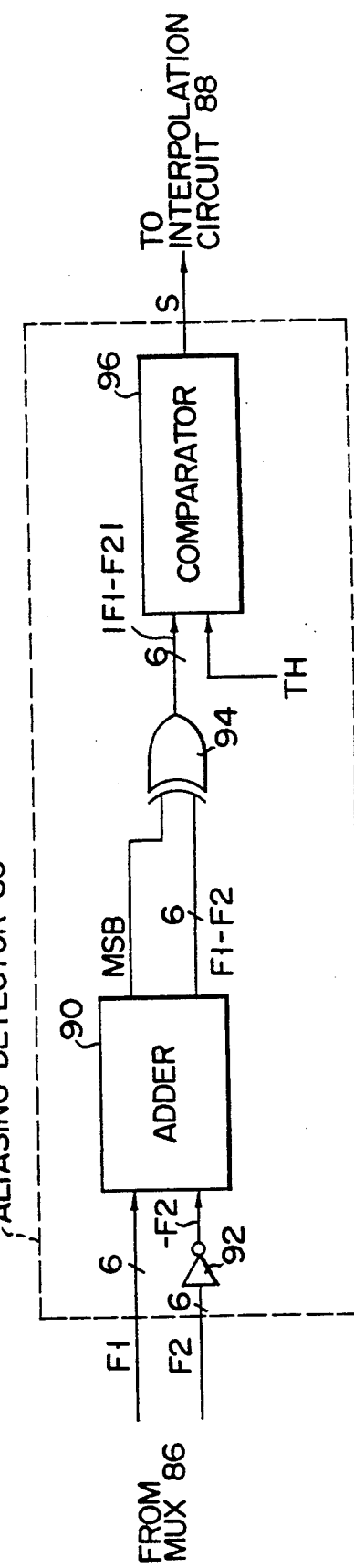
FIG. 9 is a block diagram showing in detail an aliasing detector according to the first embodiment.

FIG. 9 shows an example of the aliasing detector 86. The velocity data F1 is directly input to an adder 90, while the velocity data F2 is input to the adder 90 through an inverter 92. Since a carry input level of the adder 90 is connected to an "H" level, the inverter 92 inverts the data F2 and supplies the inverted value to the adder 90. In this manner, the adder 90 calculates "F1−F2". The 7-bit calculation output is divided into an MSB and the other 6 bits, and these are supplied to an EX-OR gate circuit 94. The EX-OR gate circuit 94 calculates the EX-OR values of the MSB and each of the lower 6 bits.

The output (6 bits) of the EX-OR gate circuit 94 is supplied to a first input terminal of a comparator 96. A second input terminal of the comparator 96 receives the above-mentioned threshold level TH. The output of the comparator 96 is delivered to the interpolation circuit 88 as an aliasing detection signal S. The aliasing detection signal S has an "H" level when aliasing is detected, and it has an "L" level when aliasing is not detected.

In accordance with the detection signal S from the aliasing detector 96, the interpolation circuit 88 interpolates the flow velocity data of an intermediate frame based on the flow velocity data F1 and F2 of the second and first frames prior to the present frame. The interpolation circuit 88 has a structure, for example, as shown in FIG. 10. An aliasing detection signal S is added, as an MSB, to one of the velocity data, e.g., the velocity data F2. Then, flow velocity data F1 and F2 are multiplied by a coefficient (=0.5 in the present embodiment) by multipliers 100 and 102, and the multiplied values are added by an adder 104. The lower 6 bits of the added result are supplied to the multiplexer 84 as interpolation flow velocity data F3.

Accordingly, when the aliasing detection signal S is "0", the interpolation circuit 88 outputs an interpolation data F3=(F1+F2)/2. When the detection signal S is "1", the interpolation circuit 88 outputs F3={F1+(F2+64)}/2 (=(F1+F2')/2−64). As is shown in FIG. 5, each frame is divided into two portions, and the multiplexer 84 selects the output of the interpolation circuit 88 in the former portion and selects the output of the multiplexer 82 in the latter portion. Of the outputs from the multiplexer 82, the frame data of a new frame is selected.

FIG. 11 shows the interpolation result in the case where no aliasing is occurred. Regarding a tomogram, the first DSC 25 adds the averages the image data of two frames, irrespective of the aliasing, thereby obtaining an interpolated tomogram. The timing chart of FIG. 5 is obtained when no aliasing is occurred. For example, as shown in FIG. 11, a blood vessel portion R1 on a first frame is situated relatively on the right side, while a blood vessel portion R2 on a second frame is situated relatively on the left side. In this case, a blood vessel portion (R1+R2)/2 is situated almost at the center area on an interpolated frame between the first and second frames.

By frame-interpolating the BDF image, the display frame rate thereof can be doubled. For example, a BDF image, which conventionally has about 5 frames per second can be displayed on a monitor with the doubled 10 frames per second; thus, the displayed image is smoothed and made clearer. The occurrence/non-occurrence of aliasing is determined on the basis of the velocity data of two frames, and, on the basis of the result of determination, the interpolation processing of the velocity data is performed. Thus, an appropriate interpolation frame image can be produced.

It is generally known that the interpolated image is correct (i.e. the interpolated image is identical to the image actually sampled at the time) if the sampled original signal meets the sampling theorem.

According to the first embodiment, a color flow mapping image obtained by detecting the intensity of reflected ultrasonic waves and the Doppler shift is frame-interpolated, whereby the frame rate of the color flow mapping image display can be increased, and the dynamic image display of the color flow mapping image can be seen naturally. In addition, if the aliasing of blood flow is detected, the flow velocity data is frame-interpolated with the aliasing taken into account. Therefore, appropriate frame interpolation is carried out.

A second embodiment of the present invention will now be described. The description of the structural elements, which have already been mentioned in the first embodiment, is omitted. In the first embodiment, one intermediate frame was interpolated on the basis of two frames, thereby doubling the display frame rate. In the second embodiment, three intermediate frames are interpolated on the basis of two frames, thereby increasing the display frame rate four times.

Figure 12:
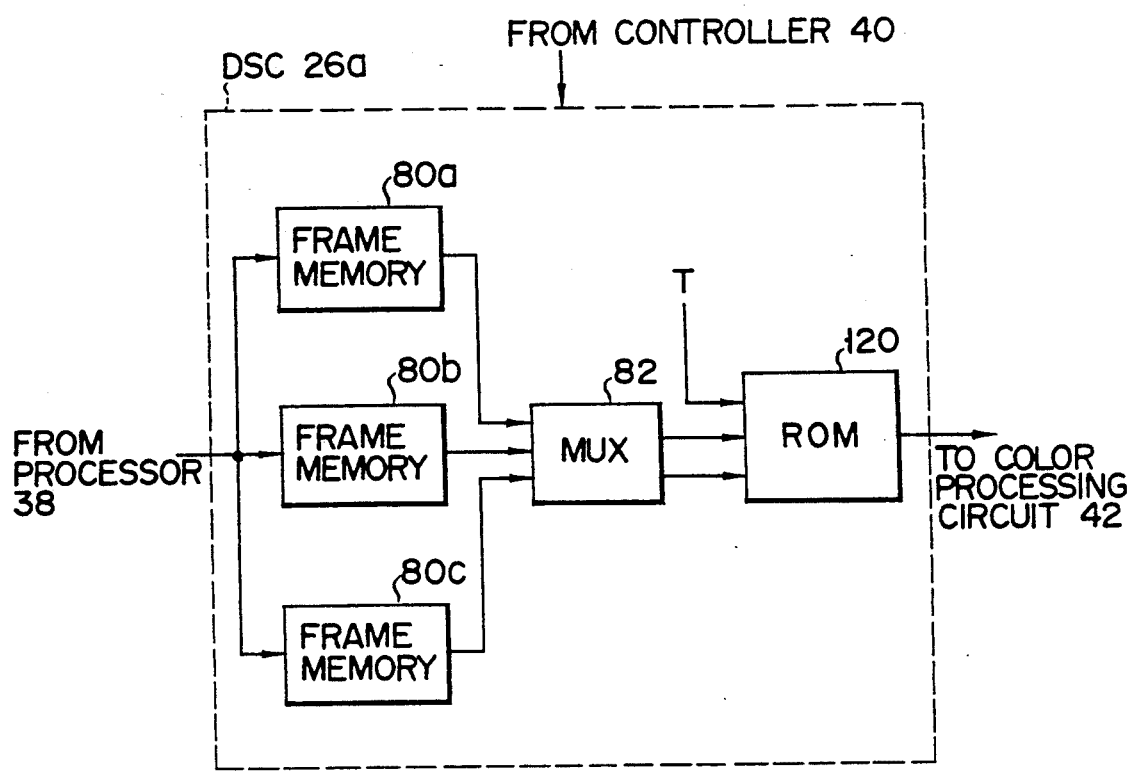
FIG. 12 is a block diagram showing in detail a blood flow data DSC which constitutes a main part of a second embodiment of the invention.

FIG. 12 is a block diagram showing a DSC 26a for blood flow data according to the second embodiment. The second embodiment differs from the first embodiment in that the aliasing detector 86, interpolation circuit 88, and multiplexer 84 of the first embodiment are replaced by a read only memory (ROM) 120, and in that a 2-bit switching signal T representing each of four divisions, into which one frame period is divided, is delivered from the controller 40 to the ROM 120. The ROM 120 is formed of, for example, 16K × 8 bit memory, and performs the same function as the detection of aliasing, the frame-interpolation, and the control of multiplexer 84, thereby finding interpolation values of velocity data. Specifically, the ROM 120 receives 6-bit velocity data F1 and F2 of two frames and 2-bit switching signal T, and generates the following 6-bit interpolation data for every ¼ frame, in accordance with the difference between data F1 and F2, the relationship in magnitude between data F1 and F2. The ROM 120 has a table denoting all of the combinations of the inputs and the outputs. In other words, the controller 40 generates, in every ¼ frame, the switching signal T varying in the order of "00", "01", "10", "11", "00", ...

Figure 13:
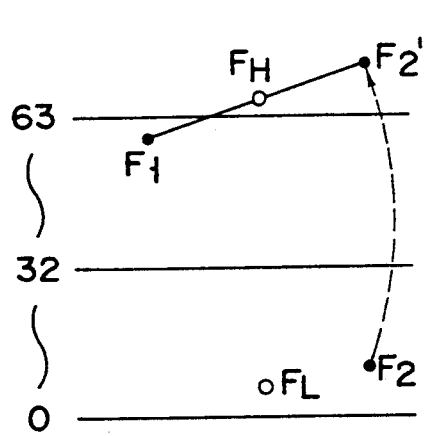
FIG. 13 shows a first aliasing detected in the second embodiment.

(1) Where F1≧F2 and |F1−F2|>TH, that is, aliasing shown in FIG. 13 has occurred:

a. when the switching signal T is "00", the lower 6 bits of {3F1+(F2+64)}/4 are output;

b. when the switching signal T is "01", the lower 6 bits of {F1+(F2+64)}/2 are output;

c. when the switching signal T is "10", the lower 6 bits of {F1+3(F2+64)}/4 are output; and d. when the switching signal T is "11", F2 is output.

Figure 14:
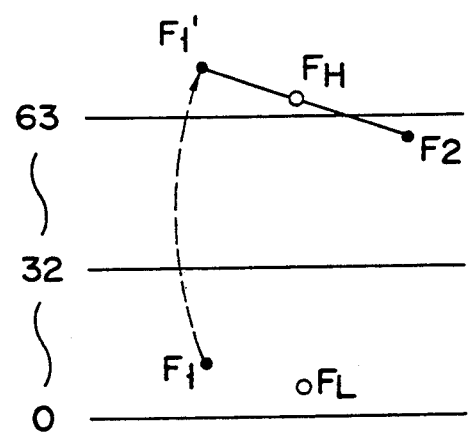
FIG. 14 shows a second aliasing detected in the second embodiment.

(2) Where F1<F2 and |F1−F2|>TH, that is, aliasing shown in FIG. 14 has occurred:

a. when the switching signal T is "00", the lower 6 bits of $\{3(F1+64)+F2\}/4$ are output;

b. when the switching signal T is "01", the lower 6 bits of $\{(F1+64)+F2\}/2$ are output;

c. when the switching signal T is "10", the lower 6 bits of $\{(F1+64)+3F2\}/4$ are output; and d. when the switching signal T is "11", F2 is output.

(3) Where $|F1-F2| \leq TH$, that is, aliasing has not occurred:

a. when the switching signal T is "00", the lower bits of $(3F1+F2)/4$ are output;

b. when the switching signal T is "01", the lower 6 bits of $(F1+F2)/2$ are output;

c. when the switching signal T is "10", the lower 6 bits of $(F1+3F2)/2$ are output; and d. when the switching signal T is "11", F2 is output.

According to the second embodiment, the velocity data of two frames are weighted and averaged, thereby frame-interpolating the flow velocity data with the display frame rate increased four times. Accordingly, the number of frames displayed is increased four times, compared to the prior art, and the BDF image are further smoothed and clarified and are dynamically varied. Like in the first embodiment, the occurrence/non-occurrence of aliasing is determined on the basis of the difference between the velocity data of two frames, and the interpolation processing is performed according to the result of determination. Thus, an appropriate interpolation frame BDF image can be produced. In the first embodiment, too, the frame interpolation can be carried out with the display frame rate increased four times. In this case, the coefficients of the multipliers 100 and 102 of the interpolation circuit 88 shown in FIG. 10 may be altered by using a ROM in every ¼ frame, as described above, and the multiplexer 84 may be omitted, with the output of the interpolation circuit 88 being employed as an output from the DSC 26. In this case, the coefficient of the multiplier 100 is set to 0.75, 0.5, 0.25, and 0 when the switching signal T is "00", "01", "10", and "11" and the coefficient of the multiplier 102 is set to 0.25, 0.5, 0.75, and 1.0 when the switching signal T is "00", "01", "10", and "11". Inversely, in the DSC 26 of the first embodiment, the ROM 120 may be substituted for the aliasing detector 86, interpolation circuit 88, and multiplexer 84.

A third embodiment of the invention will now be described. In the case where the frame interpolation is carried out according to the above embodiments, "colorless phenomenon" (described below) hardly occurs in the frame obtained by interpolation, whereas "colorless phenomenon" often occurs in the original frame. It is considered that "colorless phenomenon" is based on a lack of the Doppler shift component due to the phase interference of the ultrasonic waves.

According to the third embodiment, in order to prevent the "colorless phenomenon" of the original image, the velocity data of the original frame is subjected to smoothing processing. FIG. 15 is a block diagram showing a DSC 26b for flow velocity data, according to the third embodiment. The third embodiment differs from the first embodiment only in that the outputs F1 and F2 of the multiplexer 82 are supplied to the first and second input terminals of the multiplexer 84 through a smoothing circuit 130.

Figure 16:
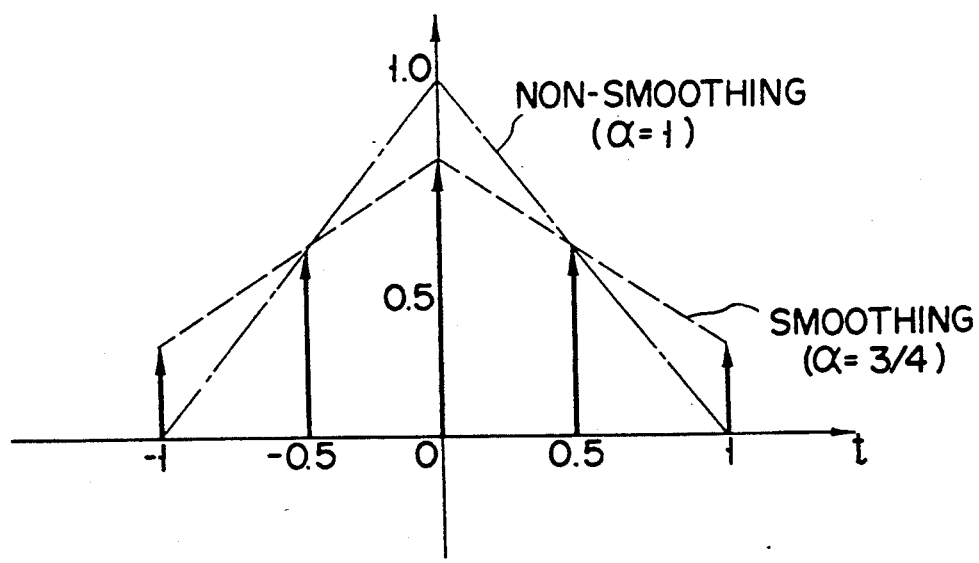
FIG. 16 illustrates the effect of smoothing according to the third embodiment.
Figure 17:
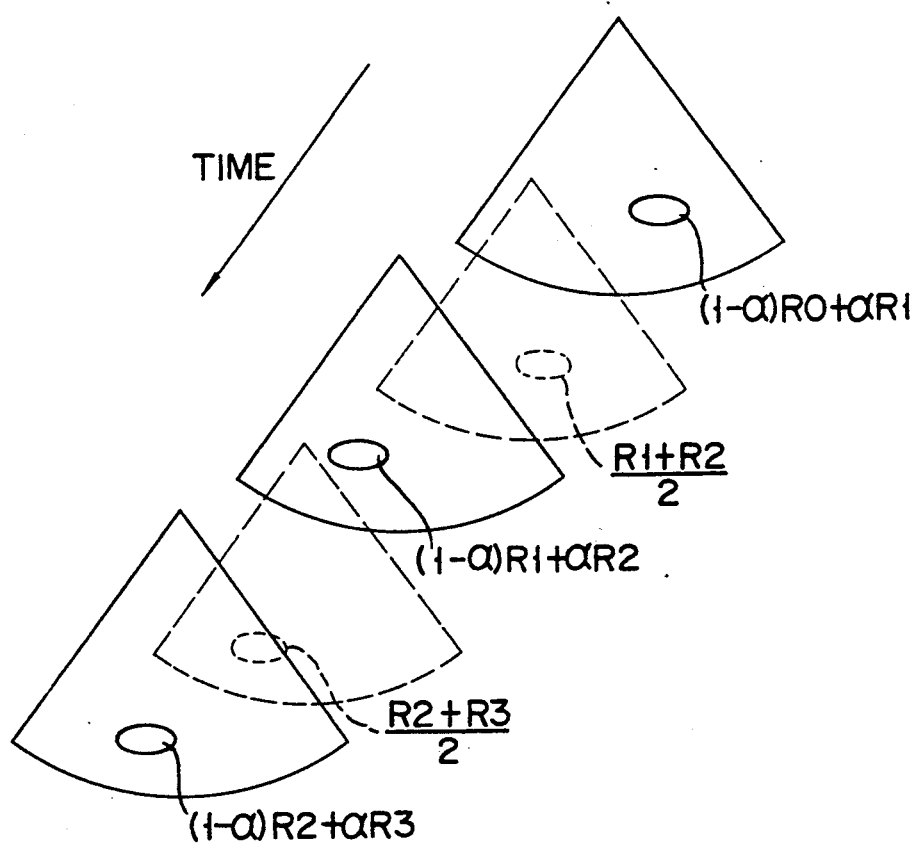
FIG. 17 illustrates the result of interpolation according to the third embodiment.

Simultaneously with the interpolation processing by the interpolation circuit 88, the smoothing circuit 130 performs a smoothing processing, e.g., $(1-\alpha)R1+\alpha R2$ for flow velocity data R1 and R2 of the second and first frames prior to the present frame, thereby generating interpolation flow velocity data. By virtue of the simultaneous processing by the interpolation circuit 88 and smoothing circuit 130, the characteristic of the smoothing function h(t) in relation to time t, in the case where the smoothing factor $\alpha = \frac{3}{4}$, is shown by a broken line in FIG. 16. On the other hand, the characteristic obtained only by the interpolation by the interpolation circuit 88, without smoothing processing, is indicated by a dot-and-broken line in FIG. 16. The timing chart of the third embodiment is obtained by modifying the chart of FIG. 5 of the first embodiment, such that the original data R2, R3, ... output from the multiplexer 84 are changed to smoothing data $(1-\alpha)R1+\alpha R2$, $(1-\alpha)R2+\alpha R3$, ... FIG. 17 shows output data from the DSC 26b for flow velocity data according to the third embodiment.

According to the third embodiment, since "colorless phenomenon" of the original frame can be prevented and the "colorless phenomenon" of the interpolated frame hardly occurs by nature, the disparity in appearance between the interpolated frame and the original frame can be prevented.

Like the second embodiment in relation to the first embodiment, the third embodiment can be further improved. In the third embodiment, one intermediate frame is interpolated on the basis of two frames, thereby doubling the display frame rate. A description will now be given of a fourth embodiment wherein the intermediate three frames are interpolated on the basis of two frames. The block diagram of the fourth embodiment is omitted, since it is identical to FIG. 12 showing the second embodiment. However, the table of the ROM differs. In the fourth embodiment, the ROM within the DSC for flow velocity data generates the following 6-bit interpolation velocity data in every ¼ frame, in accordance with flow velocity data F1 and F2 of two 6-bit frames and a 2-bit switching signal T.

(1) Where $F1 \geq F2$ and $|F1-F2| > TH$, that is, aliasing shown in FIG. 13 is occurred:

a. when the switching signal T is "00", the lower 6 bits of $\{(1+2\alpha)F1+(3-2\alpha)(F2+64)\}/4$ are output;

b. when the switching signal T is "01", the lower 6 bits of $(F1+(F2+64)\}/2$ are output;

c. when the switching signal T is "10", the lower 6 bits of $\{(3-2\alpha)F1+(1+2\alpha)(F2+64)\}/4$ are output; and d. when the switching signal T is "11", the lower 6 bits of $(1-\alpha)F1+\alpha(F2+64)$ are output.

(2) Where $F1 < F2$ and $|F1-F2| > TH$, that is, aliasing shown in FIG. 14 is occurred:

a. when the switching signal T is "00", the lower 6 bits of $\{(1+2\alpha)(F1+64)+(3-2\alpha)F2\}/4$ are output;

b. when the switching signal T is "01", the lower 6 bits of $\{(F1+64)+F2\}/2$ are output;

c. when the switching signal T is "10", the lower 6 bits of $\{(3-2\alpha)(F1+64)+(1+2\alpha)F2\}/4$ are output; and d. when the switching signal T is "11", the lower 6 bits of $(1-\alpha)(F1+64)+\alpha F2$ are output.

(3) Where $|F1-F2| \leq TH$, that is, aliasing is not occurred:

a. when the switching signal T is "00", the lower 6 bits of $\{(1+2\alpha)F1+(3-2\alpha)F2\}/4$ are output;

b. when the switching signal T is "01", the lower 6 bits of $(F1+F2)/2$ are output;

c. when the switching signal T is "10", the lower 6 bits of $\{(3-2\alpha)F1+(1+2\alpha)F2\}/4$ are output; and d. when the switching signal T is "11", the lower 6 bits of $(1-\alpha)F1+\alpha F2$ are output.

According to the fourth embodiment, the data of two frames are weighted and averaged, thereby performing frame-interpolation with the display frame rate increased four times. Accordingly, the number of frames displayed is increased four times, compared to the prior art, and the BDF image is further smoothed and clarified. Like in the third embodiment, the occurrence/nonoccurrence occurrence of aliasing is determined on the basis of the difference between the velocity data of two frames, and the interpolation processing is performed according to the result of determination. Thus, an appropriate interpolation frame image can be produced. By smoothing the original frame, the "colorless phenomenon" of the original frame can be prevented, and the disparity in appearance between the interpolated frame and the original frame can be prevented.

In the third embodiment, too, the frame interpolation can be carried out with the frame rate increased four times. In this case, the coefficients of the multipliers 100 and 102 of the interpolation circuit 88 shown in FIG. 10 may be altered in every ¼ frame, as described above, and the multiplexer 84 may be omitted, with the output of the interpolation circuit 88 being employed as an output from the DSC 26.

As has been described above, according to the present invention, the color Doppler image composed of tomographic data and two-dimensional blood flow data is frame-interpolated, thereby acquiring color Doppler data of the intermediate frame between the original frames. Thus, the number of frames displayed is increased several times, compared to the prior art, and the sequential transition of color Doppler images is smoothed and made clearer.

Where aliasing of blood flow has been detected, the flow velocity data is interpolated with the aliasing taken into account. Therefore, there is provided an ultrasonic diagnosis apparatus capable of producing appropriately interpolated frames.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

For example, in the above embodiments, tomographic data and blood flow data are scan-converted by separate DSCs and subjected to interpolation processing; however, both data may be synthesized into a color Doppler image, and then the color Doppler image is subjected to scan conversion and interpolation. The detailed description is given of the BDF image of the color Doppler image which is obtained by coloring a blood flow part on a tomographic image (B-mode image); however, this invention is applicable to the display of only the tomographic image in which no blood flow is colored and no Doppler shift is detected. In this case, since it is not necessary to consider the aliasing, it would suffice to use the interpolation circuit only. Though the above mentioned interpolation is a liner interpolation using two frames, higher-order interpolation system using four frames or more can be applicable. In addition, this invention is applicable to the BDF/FFT image in which an FFT image is added to the BDF image.

What is claimed is:

1. An ultrasonic diagnosis apparatus comprising:
   ultrasonic wave transmitting/receiving means for scanning a subject with ultrasonic waves, and receiving reflected ultrasonic waves, the ultrasonic waves being transmitted several times in each direction relating to a pulse ultrasonic wave;
   image producing means for detecting an intensity and Doppler shift of the reflected ultrasonic waves and producing color flow mapping images at a given interval by coloring a blood flow portion in a tomogram of the subject in accordance with a value and polarity of the Doppler shift;
   detecting means for detecting an aliasing on the basis of a change in the Doppler shift in the color flow mapping images of two frames; and
   interpolating means, connected to said detecting means, for interpolating an intermediate frame between two frames of the color flow mapping images produced by said image producing means, thereby producing an interval between frames which is shorter than the given interval, wherein a value of the Doppler shift included in the two frames used for the frame-interpolating processing is compensated for when aliasing is detected by said detecting means.

2. The apparatus according to claim 1, further comprising means for alternately displaying the color flow mapping image produced by said image producing means and an interpolated image obtained by said interpolating means.

3. The apparatus according to claim 1, further comprising means for smoothing the color flow mapping image produced by the image producing means and means for alternately displaying a smoothed color flow mapping image obtained by said smoothing means and an interpolated image obtained by said interpolating means.

4. The apparatus according to claim 1, wherein said interpolating means comprises means for interpolating a plurality of frames of the color flow mapping image between two frames of the color flow mapping images produced by said image producing means, and which further comprises means for sequentially displaying the color flow mapping image produced by said image producing means and interpolated images obtained by said interpolating means.

5. The apparatus according to claim 1, wherein said interpolating means comprises means for interpolating a plurality of frames of the color flow mapping image between two frames of the color flow mapping images produced by said image producing means, and which means for smoothing the color flow mapping image produced by the image producing means and means for sequentially displaying a smoothed color flow mapping image obtained by said smoothing means and interpolated images obtained by said interpolating means.

6. The apparatus according to claim 1, wherein said detecting means comprises means for detecting the occurrence of aliasing when the directions of the corresponding blood flows in the two color flow mapping images are opposite and the difference in velocity between the corresponding blood flows is greater than or equal to a predetermined value.

7. The apparatus according to claim 1, wherein said interpolating means comprises means for processing flow velocity data to compensate for aliasing prior to performing interpolation calculation when said detecting means detects aliasing.

8. The apparatus according to claim 1, wherein said first interpolating means averages tomograms of at least two frames and produces at least one interpolated tomogram, and said second interpolating means averages blood flow data of the at least two frames and produces at least one interpolated blood flow data.

9. The apparatus according to claim 8, wherein said first interpolating means comprises first means for multiplying tomograms of at least two frames by respective coefficients and second means for adding together multiplication results obtained by said first means to produce at least one interpolated tomogram, and said second interpolating means comprises third means for multiplying blood flow data of the at least two frames by respective coefficients and fourth means for adding together multiplication results obtained by said third means to produce at least one interpolation blood flow data.

10. An ultrasonic diagnosis apparatus comprising:
ultrasonic wave transmitting/receiving means for scanning a subject with ultrasonic waves, and receiving reflected ultrasonic waves, the ultrasonic waves being transmitted several times in each direction relating to a pulse ultrasonic wave;
tomogram producing means for detecting an intensity of the reflected ultrasonic waves and producing a monochromatic tomogram of the subject;
Doppler shift detecting means for detecting Doppler shift of the reflected ultrasonic waves and obtaining blood flow data representing a velocity and direction of blood flow in the tomogram;
first interpolating means for receiving the tomographic images produced by said tomogram producing means, interpolating a tomogram between two tomograms produced by said tomogram producing means, and outputting the tomogram produced by said tomogram producing means and an interpolated tomogram as an output image;
detecting means for detecting an aliasing of the blood flow data on the basis of a change in the blood flow data of two frames of the tomograms produced by said tomogram producing means;
second interpolating means for receiving the blood flow data obtained by said Doppler shift detecting means, interpolating blood flow data between blood flow data of two frames of the tomograms produced by said tomogram producing means, and outputting the blood flow data obtained by said Doppler shift detecting means and the interpolated blood flow data, wherein a value of the Doppler shift included in the two frames used for the frame-interpolating processing is compensated for when a Doppler shift is detected by said Doppler shift detecting means; and
display means for receiving the output image from the first interpolating means and the output blood flow data from said second interpolating means and displaying a color Doppler image by coloring the output image of the first interpolating means in accordance with the output blood flow data of the second interpolating means.

11. The apparatus according to claim 10, wherein said second interpolating means includes smoothing means for smoothing the blood flow data from said Doppler shift detecting means, and outputting smoothed blood flow data and interpolated blood flow data to said display means.

12. The apparatus according to claim 11, wherein said smoothing means comprises first means for multiplying the blood flow data of the first frame prior to the present frame by a first predetermined value, second means for multiplying the blood flow data of the second frame prior to the present frame by a second predetermined value, and means for adding together multiplication results obtained by said first and second multiplying means.

13. The apparatus according to claim 10, wherein said first interpolating means averages two frames of tomograms and produces one interpolated tomogram intermediate of the two frames of tomograms, and said second interpolating means averages blood flow data of the two frames of tomograms and produces an interpolated blood flow data intermediate of the blood flow data of the two frames.

14. The apparatus according to claim 10, wherein said first interpolating means at least two frames and produces at least one interpolated tomogram, and said second interpolating means at least two frames and produces at least one interpolated blood flow data.

15. The apparatus according to claim 14, wherein said first interpolating means comprises first means for multiplying tomograms of at least two frames by respective coefficients and second means for adding together multiplication results obtained by said first means to produce at least one interpolated tomogram, and said interpolating means comprises third means for multiplying blood flow data of the at least two frames by respective coefficients and fourth means for adding together multiplication results obtained by said third means to produce at least one interpolated blood flow data.

16. The apparatus according to claim 10, wherein said second interpolating means includes:
three frame memories;
means for sequentially inputting into said three frame memories, in units of a frame, outputs from the Doppler shift detecting means, wherein said frame memories change the data scan order between the time of input and the time of output so that one of the frame memories is in a write mode while two of the frame memories are in a read mode;
a first multiplexer for selecting two output signals from two of said three frame memories which are not in the write mode;
interpolation signal producing means for producing an interpolated signal by frame-interpolating the two signals selected by the first multiplexer in accordance with the result of aliasing detection; and
a second multiplexer for receiving the output from the first multiplexer and the interpolated signal, and alternately outputting the data of a new frame output from the first multiplexer and the interpolated signal, and wherein said aliasing detecting means comprises means for detecting the aliasing on the basis of the two signals selected by the first multiplexer.

17. An ultrasonic diagnosis apparatus comprising:
ultrasonic wave transmitting/receiving means for scanning a subject with ultrasonic waves, and receiving reflected ultrasonic waves, the ultrasonic waves being transmitted several times in each direction relating to a pulse ultrasonic wave;
Doppler shift detecting means for determining Doppler shift of the reflected ultrasonic waves and obtaining blood flow data representing a velocity and direction of a blood flow in the tomogram;

detecting means for detecting an aliasing on the basis of a change in the Doppler shift between two blood flow data; and interpolating means for interpolating blood flow data between two blood flow data produced by said Doppler shift detecting means, thereby increasing a display rate of the blood flow data, wherein a value of the Doppler shift in the two blood flow data used in the interpolating processing is compensated for when aliasing is detected by said aliasing detecting means.

18. An ultrasonic diagnosis apparatus comprising:

ultrasonic wave transmitting/receiving means for repeatedly scanning ultrasonic waves at a given interval in a given cross-sectional area of a subject, and receiving the reflected ultrasonic waves;

detecting means for detecting an intensity of the reflected ultrasonic waves and obtaining tomographic images of the subject; and interpolating means for interpolating a tomographic image between two tomographic images obtained by said detecting means to produce an interval between the two tomographic images which is shorter than the given interval, thereby increasing a display rate of the tomographic images.

19. An ultrasonic diagnosis apparatus comprising:

ultrasonic wave transmitting/receiving means for scanning a subject with ultrasonic waves, and receiving reflected ultrasonic waves, the ultrasonic waves being transmitted several times to each direction relating to a pulse ultrasonic wave;

image producing means for detecting an intensity and Doppler shift of the reflected ultrasonic waves and producing color flow mapping images at a given interval by coloring a blood flow portion in a tomogram of the subject in accordance with a value and polarity of the Doppler shift;

interpolating means for interpolating an intermediate frame of the color flow mapping image between two frames of the color flow mapping images produced by said image producing means to produce an interval between frames of the color flow mapping images which is shorter than the given interval.

* * * * *

UNITED STATES PATENT AND TRADEMARK OFFICE
CERTIFICATE OF CORRECTION

PATENT NO. :   5,188,113
DATED      :   February 23, 1993
INVENTOR(S):   Takeshi Sato et al.

It is certified that error appears in the above-identified patent and that said Letters Patent is hereby corrected as shown below:

Abstract, title Page, line 19, delete "for".

Claim 5, column 12, line 52, befor "means " insert --further comprises--.

Claim 9, column 13, line 17, change "interpolation" to --interpolated--.

Signed and Sealed this

Twenty-sixth Day of April, 1994

Attest:

BRUCE LEHMAN

*Attesting Officer*          *Commissioner of Patents and Trademarks*